(12) United States Patent
Bayrock et al.

(10) Patent No.: US 6,353,657 B1
(45) Date of Patent: Mar. 5, 2002

(54) IMAGE REDIRECTION AND OPTICAL PATH FOLDING

(75) Inventors: Terrence G. Bayrock, Sherwood Park; Richard N. Hull, Calmar, both of (CA); Bruno Wuest, Mobile, AL (US)

(73) Assignee: Wuestec Medical, Inc., Theodore, AL (US)

( * ) Notice: Subject to any disclaimer, the term of this patent is extended or adjusted under 35 U.S.C. 154(b) by 0 days.

(21) Appl. No.: 09/449,046

(22) Filed: Nov. 24, 1999

(Under 37 CFR 1.47)

Related U.S. Application Data (60) Provisional application No. 60/110,099, filed on Nov. 27, 1998.

(51) Int. Cl.[7] .................................................. A61B 6/14
(52) U.S. Cl. ...................................... 378/98.3; 378/98.8
(58) Field of Search ........................... 378/62, 44, 98.8, 378/98.3

(56) References Cited

U.S. PATENT DOCUMENTS

| | | | |
|---|---|---|---|
| 3,860,817 A | 1/1975 | Carmean | 250/320 |
| 4,412,346 A | 10/1983 | Takenouti et al. | 378/181 |
| 4,684,565 A | 8/1987 | Abeles et al. | 428/220 |
| 4,761,805 A | 8/1988 | Sebring | 378/181 |
| 4,821,727 A | 4/1989 | Levene et al. | 128/653 |
| 4,890,313 A | 12/1989 | Lam et al. | 378/189 |
| 4,924,487 A | 5/1990 | Nishiki | 378/190 |
| 4,979,198 A | 12/1990 | Malcolm et al. | 378/102 |
| 4,987,307 A | 1/1991 | Rizzo et al. | 250/368 |
| 4,995,068 A | 2/1991 | Chou et al. | 378/189 |
| 5,090,042 A | 2/1992 | Bejjani et al. | 378/99 |
| 5,211,165 A | 5/1993 | Dumoulin et al. | 128/653.1 |
| 5,864,146 A * | 1/1999 | Karellas | 378/169 |
| 6,038,286 A * | 3/2000 | Wageli | 378/98.3 |

FOREIGN PATENT DOCUMENTS

CA 2179616 7/1994 ........... G03B/41/16

* cited by examiner

*Primary Examiner*—Drew Dunn
(74) *Attorney, Agent, or Firm*—Fulbright & Jaworski L.L.P.

(57) ABSTRACT

A system and method for digital x-ray imaging which utilizes optical path folding by redirecting the image more than once before providing it to an imaging sensor is disclosed. In the preferred embodiment, multiple redirection or folding of light is achieved by multiple redirecting elements. An imaging sensor is preferably used to capture the image from the multiple redirecting elements. Such an imaging sensor may comprise a photosensitive plate and a lens assembly.

28 Claims, 7 Drawing Sheets

FIG. 6

IMAGE REDIRECTION AND OPTICAL PATH FOLDING

RELATED APPLICATIONS

The present application claims the benefit of co-pending U.S. Provisional Application No. 60/110,099, filed Nov. 27, 1998, the disclosure of which is incorporated herein by reference. The present application is related to concurrently filed U.S. patent application Ser. No. 09/449,172 filed Nov. 24, 1999, entitled "DIGITAL HIGH RESOLUTION X-RAY IMAGING", the disclosure of which is incorporated herein by reference. The present application is also related to concurrently filed U.S. patent application Ser. No. 09/449,174 filed Nov. 24, 1999, entitled "OPTICAL DISTORTION CORRECTION IN DIGITAL IMAGING", the disclosure of which is incorporated herein by reference. The present application is also related to concurrently filed U.S. patent application Ser. No. 09/449,173 filed Nov. 24, 1999, entitled "AUTOMATIC EXPOSURE INITIATION IN A DIGITAL CCD CAMERA X-RAY IMAGER", the disclosure of which is incorporated herein by reference.

TECHNICAL FIELD

The present invention relates to image redirection in digital imaging and in particular to optical path folding in a digital x-ray imaging system.

BACKGROUND

In conventional x-ray imaging a photographic film is exposed to visible light in order to capture the image of the object being x-rayed. The x-rays are passed through the object and impinge on an imaging screen, such as a phosphor imaging screen. The phosphor imaging screen converts some of the radiation into a selected spectral component (typically visible light). The exposure of the photographic film to the spectral component from the phosphor imaging screen produces the image of the object on the photographic film.

Recent advances in x-ray imaging however have changed the focus from use of photographic films to electronic imaging sensors. Such a system is disclosed in U.S. Pat. No. 5,309,496, entitled "FILMLESS X-RAY APPARATUS AND METHOD OF USING THE SAME", issued to Winsor, which is hereby incorporated herein by reference. In the preferred embodiment of Winsor, a video camera and a frame grabber are used to provide still x-ray images.

Figure 1:
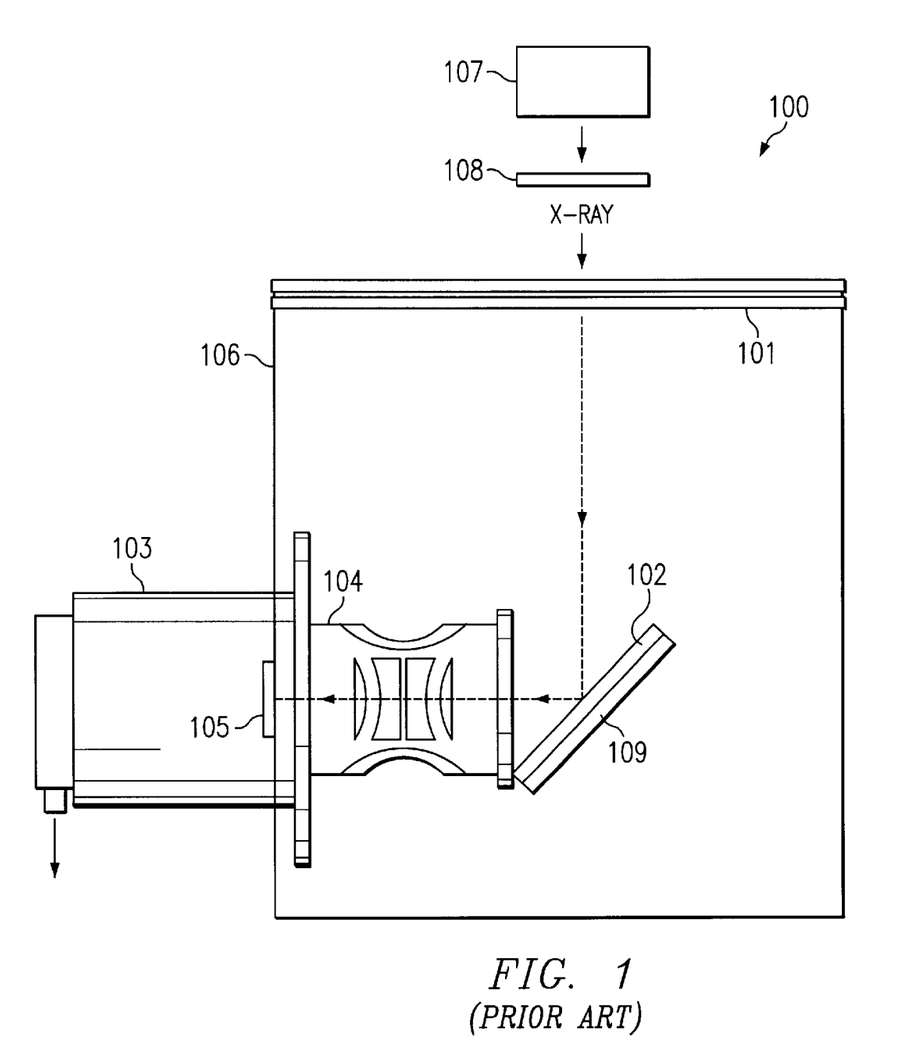
FIG. 1 represents a top view of a prior art imaging system.

An alternative electronic imaging sensor structure, like a CCD (charge coupled device) camera, as shown in FIG. 1 may also be used for x-ray imaging. FIG. 1 shows a top view of a prior art imaging system 100. Imaging system 100 comprises X-ray source 107 that emits X-rays to image object 108. Imaging system 100 comprises a camera housing 106. One side of camera housing 106 is preferably made up of a radio-transparent plastic and a phosphor imaging screen 101. In the embodiment of the prior art system shown in FIG. 1, a CCD camera 103 is positioned at another side of camera housing 106. CCD camera 103 includes a CCD chip 105 and a lens (or lens assembly) 104.

As the phosphor imaging screen 101 does not convert all the x-rays, there is some residual portion of the x-rays left in the light coming from the phosphor screen. When imaging with a sensor which may be exposed to high energy x-ray radiation, there is the potential for the imaging sensor and associated electronics to be damaged by such x-ray radiation. Moreover, the radiation energy in the light may produce undesirable image artifacts in the captured image. The prior art system shown in FIG. 1 solves this problem by redirecting the light from the phosphor imaging screen 101 in such a manner as to place the imaging sensor and its associated electronics out of the path of the x-ray radiation. The prior art imaging system shown in FIG. 1 uses a single mirror element or prism 102, including X-ray absorbing element 109, to redirect the visible light towards the imaging sensor, such as CCD camera 103. Typically, such mirrors are rectangular in shape. Therefore, in prior art systems, the light from the phosphor screen is redirected by a single mirror before being provided to the imaging sensor. This solves the problems associated with image artifacts and prevents damage to the imaging sensor that may be caused due to exposure to high energy radiation.

The size of the camera housing is dependent on the size of the lens as the housing has to be of sufficient size to accommodate the lens. Because the lens (or lens assembly) used in such a system is typically very long, the housing cannot be less than a predefined size. Moreover, the size of the lens significantly effects the overall cost of the x-ray imaging system. Furthermore, the optical distance of the CCD chip 105 from the phosphor screen 101 also depends on the lens. Therefore, the optical distance of the CCD chip from the phosphor screen also limits the size of the camera housing.

Therefore, there is a need in the art for a system and method for reducing the overall camera housing dimensions while also reducing the costs associated with digital x-ray imaging.

SUMMARY OF THE INVENTION

These and other objects, features and technical advantages are achieved by a system and method for digital imaging which utilizes optical path folding by redirecting the image more than once before providing it to an imaging sensor.

The optical distance of CCD chip 105 of FIG. 1 from the imaging screen 101 is the sum of the lengths of the lens (or lens assembly) and the optical path. The optical path is the path taken by the light source from the imaging screen to the surface of the lens. Since the optical distance is predefined, therefore for a given optical distance, by increasing the length of the optical path, the length of the corresponding lens may be reduced. This is preferably accomplished by making the light from the imaging screen, such as a phosphor imaging screen used in x-ray imaging, travel a longer distance before coming in contact with the lens surface.

The length of the optical path may be increased without increasing the dimensions of the camera housing by redirecting the light from the phosphor screen more than once before it comes in contact with the lens surface. Thus, by redirecting the light several times within the camera housing, the length of the optical path can be increased thereby allowing reduction in the length of the lens for a given optical distance (or for a given imaging screen size). Multiple redirection of the light creates the effect of optical path folding.

Multiple redirections or folds of the light may be accomplished by using multiple redirecting elements within the camera housing. Such redirecting elements may be a mirror, a prism with a reflecting surface, or any other object capable of redirecting light. In a preferred embodiment of the present invention light from the phosphor screen is folded twice, once by using a first mirror which reflects the light to a second mirror which then redirects the light into a lens (or lens assembly) and then onto a CCD chip associated with an imaging sensor, such as a CCD camera.

The size of the housing may be further reduced by using multiple imaging sensors. Multiple imaging sensors may be used to capture different portions of a single image or imaging screen. In a preferred embodiment of the present invention, the phosphor imaging screen is divided into two portions and each portion of the screen or image is preferably captured by a different imaging sensor. Moreover, each imaging sensor preferably has at least two redirecting elements associated with it to redirect the light at least twice from the associated portion of the image. Preferably, the redirecting elements are shaped and/or positioned in such a manner so as to encompass the full field of view of the associated imaging sensor along an optical plane. In the case of multiple imaging sensors, the optical configuration used to direct the imaging rays of light onto the respective imaging sensors is an important consideration. The optical configuration should be such as to allow for overlapping fields of view for each imaging sensor so that after image capturing, different portions of the image may be stitched together, if desired, for example to create the entire image. The overlapping portions of the images provide a reference for stitching or joining together the different images.

Accordingly, it is a technical advantage of a preferred embodiment of the present invention to provide a smaller camera housing for a predefined imaging screen size.

It is another technical advantage of a preferred embodiment of the present invention that the size of the lens used can be reduced.

It is yet another technical advantage of a preferred embodiment of the present invention to reduce the cost of digital x-ray imaging due to reduction in the size of the lens.

It is still another technical advantage of a preferred embodiment of the present invention that the image does not have any artifacts.

It is still another technical advantage of a preferred embodiment of the present invention that the electronics components associated with an imaging sensor are not subjected to x-ray radiation.

It should be noted that although visible light is used as an example in the preferred embodiment, any spectral radiation may be dealt with in a similar manner with suitable reflecting and/or redirecting elements.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 2:
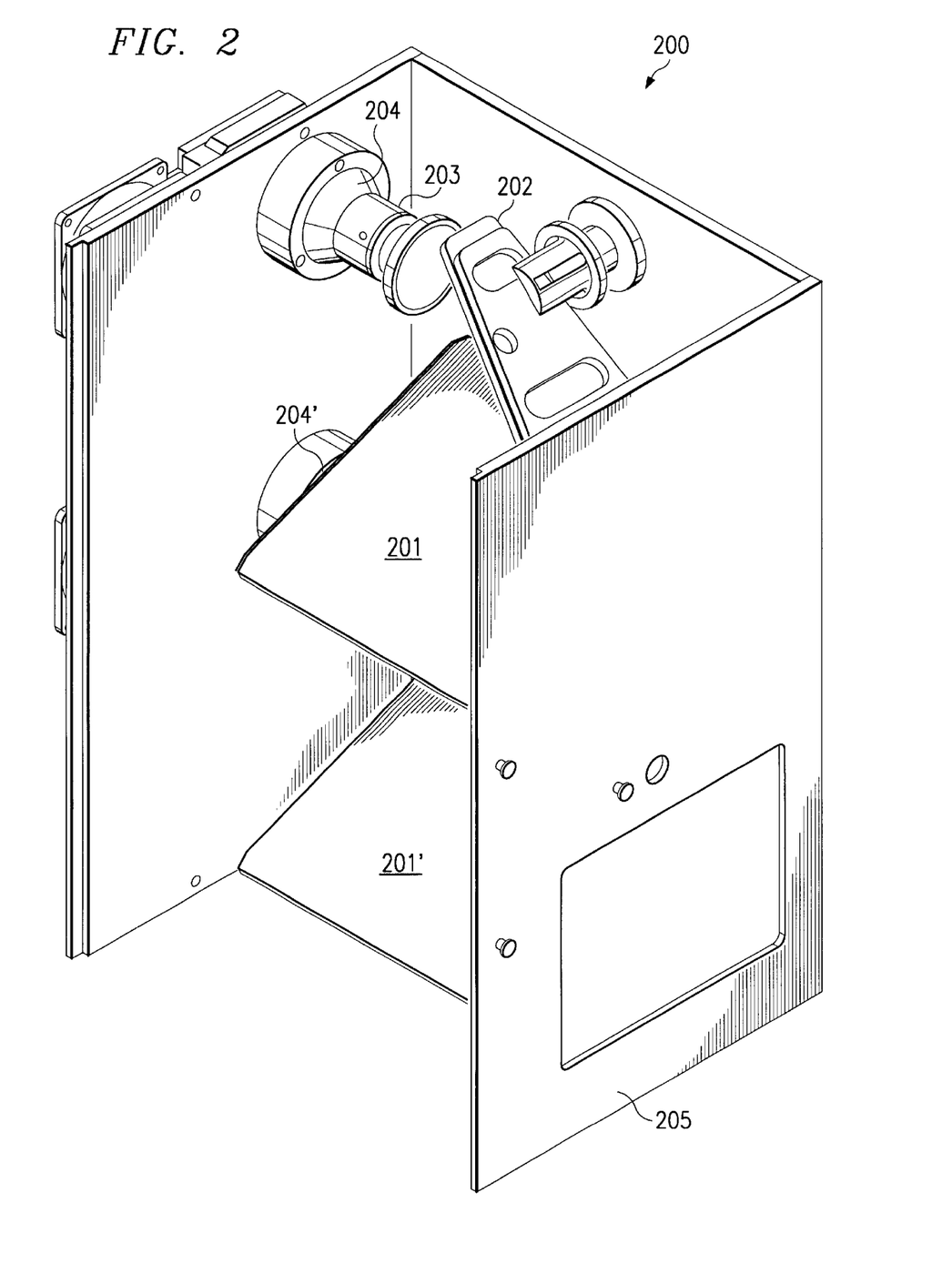
FIG. 2 represents a perspective view of a cutaway camera housing of an imaging system of a preferred embodiment.

FIG. 2 shows a perspective view of an imaging system of the preferred embodiment of the present invention. Imaging system 200 comprises a camera housing 205. The cutaway portion preferably comprises an imaging screen, for example a fluorescent phosphor screen used in x-ray imaging.

In a preferred embodiment of the present invention, the imaging screen is preferably divided into multiple portions, for example an upper portion and a lower portion. Note that 'upper' and 'lower' do not reflect the actual orientation of system 200, but rather are used to describe its appearance in FIG. 2. The upper portion of the image is preferably captured by a first subsystem of the imaging system 200 and the lower portion of the image is preferably captured by a second subsystem of the imaging system 200. The images captured by the first subsystem and the second subsystem overlap, preferably by about 20%. Thus, in the embodiment shown in FIG. 2, the first subsystem preferably captures the upper half of the imaging screen and approximately the upper 10% of the lower half of the screen. On the other hand, the second subsystem preferably captures the lower half of the imaging screen and approximately the lower 10% of the upper half of the screen. The overlap of the images captured by the first subsystem and the second subsystem allows subsequent stitching or joining of the images, if desired, for example to create the entire image.

The first subsystem includes an imaging sensor 204, which is preferably a CCD camera comprising a photosensitive plate, such as a CCD chip (not shown) and a lens (or lens assembly) 203. The first subsystem also includes a first redirecting element 201 and a second redirecting element 202. The first redirecting element 201 is preferably a front-surfaced mirror, preferably trapezoidal in shape. The front surface reflects the visible light while passing x-ray radiation. The back of the mirror is preferably coated with a substance, such as lead, to absorb any x-ray radiation. The first redirecting element 201 is preferably positioned at a 45 degree angle to the plane of the object or the imaging screen. The trapezoidal shape of mirror 201 allows the mirror to encompass the entire field of view of its associated CCD camera 204. The camera and its associated electronics components are used to acquire the image from the imaging screen. Moreover, the trapezoidal shape of the mirror allows the captured image to be rectangular in shape, thereby preventing a keystoning effect which would produce a trapezoidal image. Another advantage of using a trapezoidal mirror instead of a rectangular mirror is that the weight of a trapezoidal mirror is less than the corresponding rectangular mirror.

The second redirecting element 202 is preferably a front-surfaced mirror which is trapezoidal in shape. The trapezoidal shape of mirror 202 allows it to encompass the field of view of the CCD camera 204 when mirror 202 is positioned at a 45 degree angle to the image plane of the first redirecting element 201. The lens assembly 203 comprises of a series of lens elements used to focus the object onto imaging sensor

204. The imaging sensor and its associated electronics components are used to acquire the image from the imaging screen. The second subsystem is preferably substantially the same as the first subsystem and is described with reference to FIG. 3.

Figure 3:
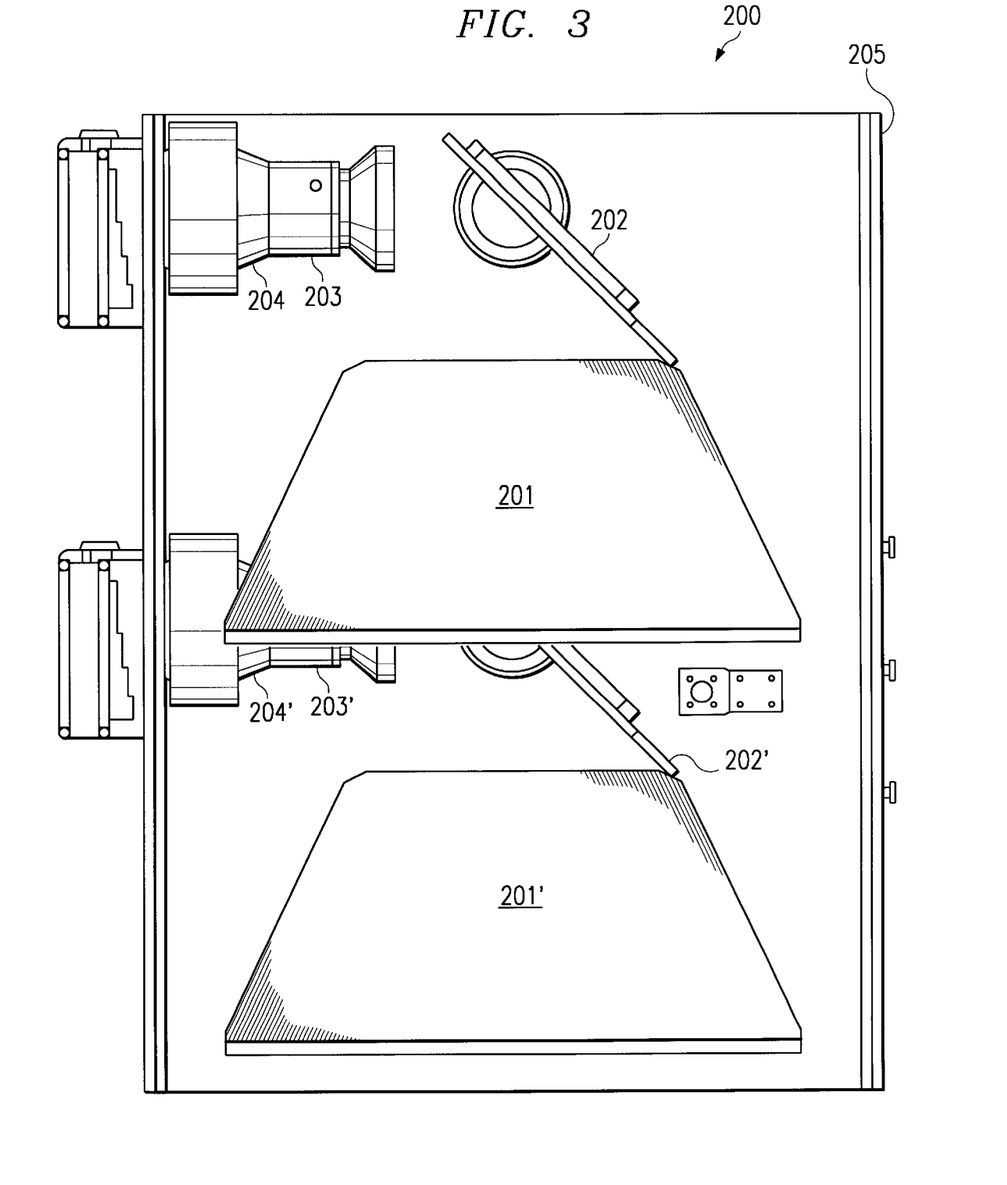
FIG. 3 represents a side view of the preferred embodiment imaging system of FIG. 2.

FIG. 3 shows a side view of the preferred embodiment imaging system of FIG. 2. As shown in FIG. 3, the second subsystem includes an imaging sensor 204', which is preferably a CCD camera comprising a CCD chip (not shown) and a lens (or lens assembly) 203'. The second subsystem also includes a first redirecting element 201' and a second redirecting element 202'. The first redirecting element 201' is preferably a front-surfaced mirror, preferably trapezoidal in shape, and is preferably positioned at a 45 degree angle to the plane of the object (i.e. the imaging screen). The trapezoidal shape of mirror 201' allows the mirror to encompass the entire field of view of its associated CCD camera 204'. The second redirecting element 202' is preferably a front-surfaced mirror which is trapezoidal in shape. The trapezoidal shape of mirror 202' allows it to encompass the entire field of view of the CCD camera 204' when mirror 202' is positioned at a 45 degree angle to the image plane of the first mirror 201'. The lens assembly 203' comprises of a series of lens element used to focus the object onto the imaging sensor 204'. The imaging sensor and its associated electronics components are used to acquire the image from the imaging screen.

Figure 4:
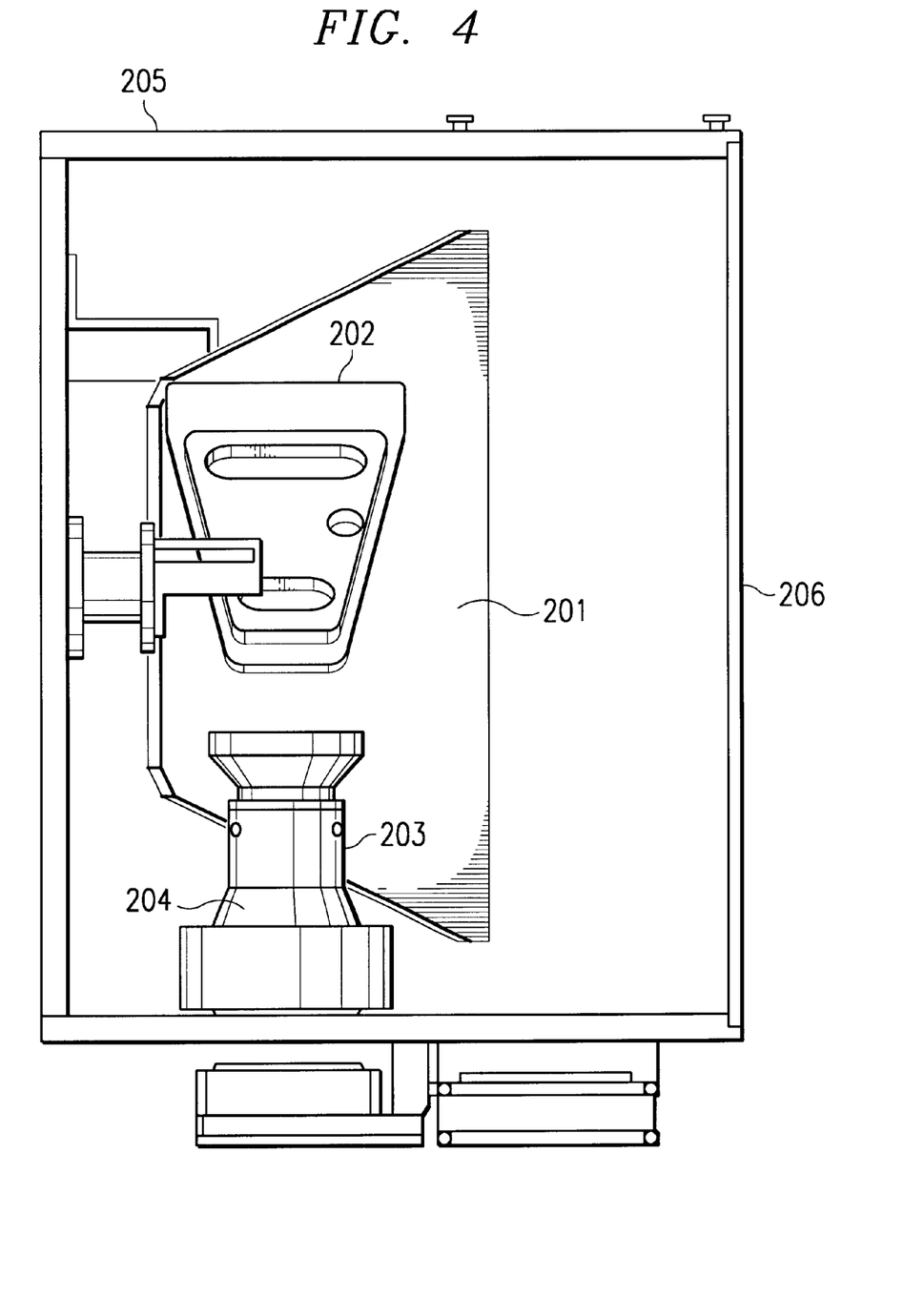
FIG. 4 represents a top plan view of the preferred embodiment imaging system.

FIG. 4 represents a top plan view of the preferred embodiment imaging system of the present invention. The top view of the first subsystem as described above with regard to FIG. 2 for capturing a portion of the imaging screen is shown. In FIG. 4, the imaging screen is shown by reference numeral 206.

In FIG. 2, light from the upper portion of the imaging screen falls on the first redirecting element 201. The mirrored surface of the redirecting element 201 reflects the light from the imaging screen to form a first redirected light. The second redirecting element 202 is positioned so that the first redirected light from the first redirecting element falls on the second redirecting element. The mirrored surface of the second redirecting element 202 redirects the first redirected light received from the first redirecting element onto the lens assembly 203 of imaging sensor 204. The lens assembly 203 comprises a series of lens element used to focus the object onto the imaging sensor 204. The imaging sensor 204, such as a digital camera, includes a photosensitive plate, such as a CCD chip, as shown in FIG. 1. The CCD chip is capable of capturing the image. Thus, the upper portion of the imaging screen is captured by CCD camera 204.

With reference to FIG. 3, light from the lower portion of the imaging screen falls on the first redirecting element 201'. The mirrored surface of the redirecting element 201' reflects the light from the imaging screen to form a first redirected light for the lower portion of the imaging screen. The second redirecting element 202' is positioned so that the first redirected light from the first redirecting element 201' falls on the second redirecting element. The mirrored surface of the second redirecting element 202' redirects the first redirected light received from the first redirecting element 201' onto the lens assembly 203' of imaging sensor 204'. Lens assembly 203' comprises a series of lens element used to focus the object onto the imaging sensor 204'. The imaging sensor 204', such as a digital camera, includes a photosensitive plate, such as a CCD chip, as shown in FIG. 1. The CCD chip is capable of capturing the image. Thus, the lower portion of the imaging screen is captured by CCD camera 204.

Figure 5A:
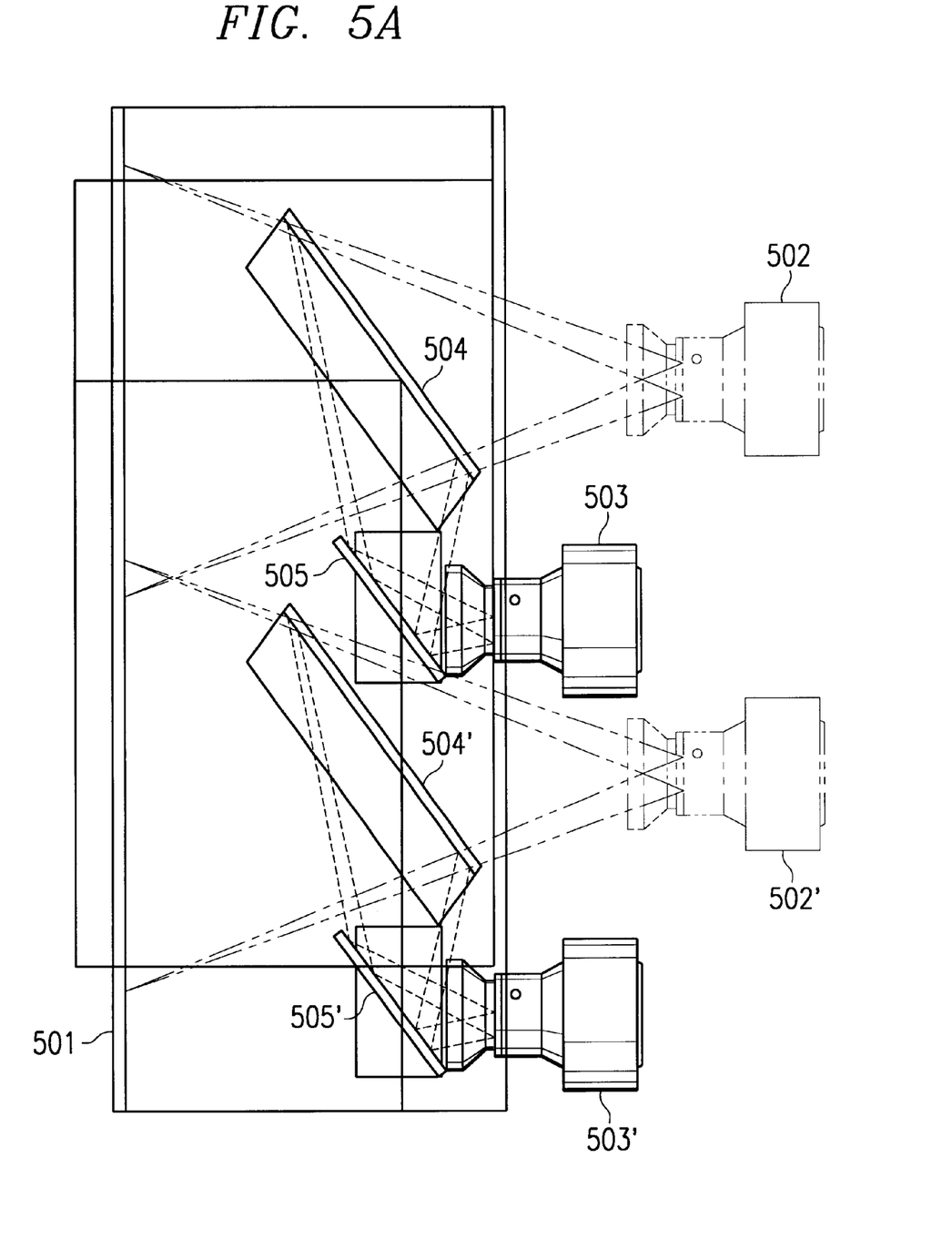
FIGS. 5A and 5B show schematic representations of an image folding path.
Figure 5B:
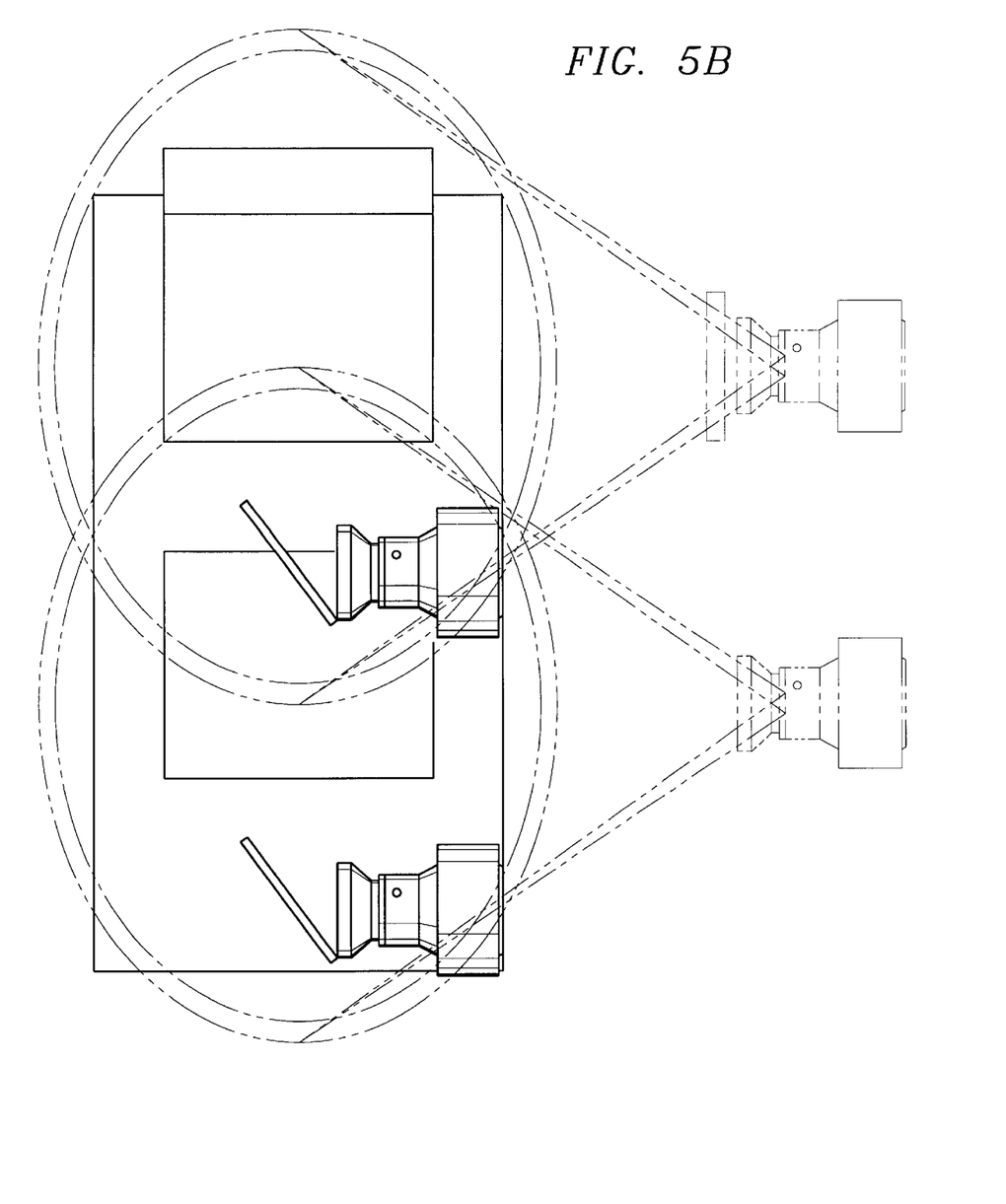

FIGS. 5A and 5B demonstrate the effect on the size of the camera housing due to the use of multiple redirecting elements. In FIGS. 5A and 5B, the prior art system is shown in phantom. In FIG. 5A, imaging sensors 502, 502' receive the image from imaging screen 501 directly without any redirection. On the other hand, in the case of imaging sensors 503, 503', light from imaging screen 501 is first redirected by mirrors 504, 504' respectively. The light from mirror 504 is further redirected by mirror 505 and fed to imaging sensor 503. Similarly, light from mirror 504' is further redirected by mirror 505' and fed to imaging sensor 503'. As can be seen from FIG. 5A an imaging system utilizing imaging sensors 502, 502' which capture the image from screen 501 without redirection would require a camera housing of dimensions greater than an imaging system utilizing imaging sensors 503, 503' which employ multiple redirection to capture the image. Moreover, as light from imaging screen 501 reaches imaging sensors 502, 502' directly, the electronic components associated with imaging sensors 502, 502' may be damaged due to high energy x-ray radiation not converted by imaging screen 501. On the other hand, as light from imaging screen 501 reaching imaging sensors 503, 503' is redirected, there is no x-ray radiation associated with it and hence the electronics components associated with imaging sensors 503, 503' would not be damaged. FIG. 5B is substantially similar to FIG. 5A and provides a top view of the camera system.

It should be noted, that the two image sensors utilized in the preferred embodiment described above have overlapping fields of view, i.e. the images captured by the two image sensors share a common portion of the imaging screen. This facilitates stitching or joining of the captured images. A system and method for joining or stitching together the different images is disclosed in the above referenced concurrently filed U.S. Patent Application entitled "DIGITAL HIGH RESOLUTION X-RAY IMAGING", the disclosure of which is incorporated herein by reference. Such a method and system for joining together different images and correcting optical distortion due to the shape of the lens or lens assembly is discussed in the above referenced concurrently filed U.S. Patent Application entitled "OPTICAL DISTORTION CORRECTION IN DIGITAL IMAGING".

By splitting the imaging screen and using multiple image sensors, the dimension of the camera housing may be reduced as each image sensor captures a smaller portion of the imaging screen. Moreover, because of multiple redirection of the light from at least one portion of the imaging screen, the length of the optical path is increased. Thus, by folding (or redirecting) the light from the imaging screen multiple times before it reaches the lens, the optical path is increased without a corresponding increase in camera housing. Therefore, the length of the lens or lens assembly may be reduced correspondingly for the particular subsystem that utilizes multiple image redirection to capture the image. Accordingly, the cost of the lens assembly may be reduced as smaller lens are cheaper than longer lens. Moreover, as the dimension of the camera housing is limited by the size of the lens, the camera housing may now be of a smaller size as the length of the lens (or lens assembly) is reduced.

Therefore, splitting of the imaging screen and use of multiple imaging sensors allows the camera housing to be smaller as each imaging sensor now captures a smaller portion of the imaging screen thereby reducing the optical distance. Moreover, optical path folding allows the camera housing to be smaller by increasing the optical path length thereby allowing a lens (or lens assembly) of smaller size to be utilized.

Figure 6:
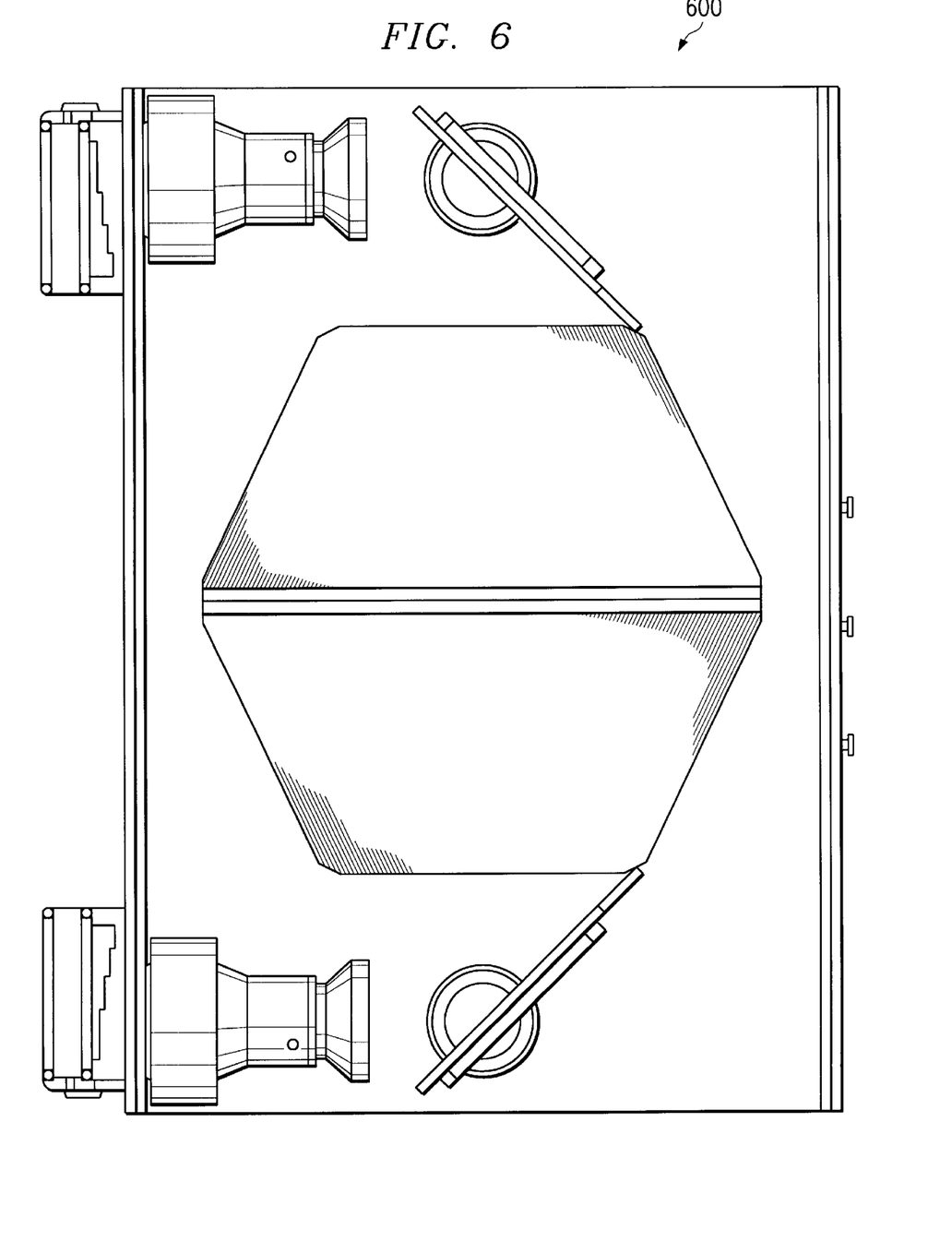
FIG. 6 represents a side view of an alternative embodiment imaging system of the present invention.

Although the present invention has been described above with regard to imaging systems as shown in FIGS. 2–4, the imaging sensors may be positioned at different locations, if desired. For example, in an alternative embodiment, the imaging sensor in the middle of the camera housing as shown in FIG. 3 may be positioned closer to the other end of the housing. In such an embodiment, the positions of the redirecting elements would be correspondingly adjusted to cover the field of view of the imaging sensors. Thus, in this embodiment of the present invention, the bottom portion of the imaging system would be a mirror image of the top portion as shown by imaging system 600 in FIG. 6.

Moreover, although the present invention has been described above with regard to splitting the imaging screen into two portions, the invention is not so limited and the imaging screen may be split into more than two portions or not split at all. Furthermore, although each subsystem has been discussed with regard to employing two redirecting elements, the invention is not so limited and if desired more than two redirecting elements may be used. Use of more than two redirecting elements may be desirable, for example, when the imaging screen is large or when it is desirable to have a smaller camera housing than that achieved by a subsystem employing two redirecting elements. By increasing the number of redirecting elements (and hence the amount of folding), in a particular subsystem, the optical path length for that particular subsystem may be increased thereby reducing the length of the lens (or lens assembly). Thus, lens assemblies of different lengths may be used in the different subsystems, if desired.

Moreover, when the imaging screen is split into two or more portions, it is not necessary that the imaging system associated with all the portions provide multiple image redirection. Depending on the size of the portions, some of the imaging systems may provide multiple redirection, while others may provide only a single redirection. For example, if an imaging screen is split into five portions, depending on the size of each portion, single or multiple redirection may be provided by the corresponding imaging system. Moreover, although the present invention has been described with regard to splitting the imaging screen into an upper portion and a lower portion, the invention is not so limited and in alternative embodiments the imaging screen may be split horizontally. In other embodiments, the imaging screen may be split both horizontally and vertically, if desired. Thus, the system may be scaled to increase the number of imaging sensors in both the horizontal and/or vertical directions depending on the particular application. Furthermore, in the present invention, due to multiple redirection by the redirecting elements, the path of light may cross itself, if desired, i.e. it is not necessary that light from the imaging screen reach the imaging sensor without crossing itself.

Moreover, although in the preferred embodiment mirrors are used as redirecting elements, the invention is not so limited, and prisms may be used for redirection. For example, a prism comprising one reflecting surface may be used as the second redirecting element discussed above, if desired. This would be specially useful if the lens assembly were located outside the camera housing instead of inside the camera housing as shown in FIGS. 2–6. Moreover, shaped mirrors (for example catadioptric lens) may be used if desired.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An x-ray apparatus for capturing an image from an imaging screen, comprising:
   a source of x-rays disposed for directing x-rays through an object, wherein said object is positioned between said x-ray source and an imaging screen, and wherein said imaging screen is disposed at least partially in the path of said x-rays passing through said object;
   a first subsystem for capturing an image from a first portion of said imaging screen, wherein said first subsystem comprises a first redirecting element and a second redirecting element for redirecting visible light from said first portion of said imaging screen onto a first imaging sensor, wherein said first portion of said imaging screen is positioned between said x-ray source and said first subsystem; and
   a second subsystem for capturing an image from a second portion of said imaging screen, wherein said second subsystem comprises a third redirecting element for redirecting light from said second portion of said imaging screen onto a second imaging sensor.

2. The x-ray apparatus of claim 1, wherein said imaging screen is a fluorescent phosphor screen.

3. The x-ray apparatus of claim 1, wherein said first redirecting element is positioned at a 45 degree angle to a plane of said imaging screen.

4. The x-ray apparatus of claim 1, wherein said second redirecting element is adapted to encompass a field of view of said first imaging sensor when said second redirecting element is positioned at a 45 degree angle to an image plane of said first redirecting element.

5. The x-ray apparatus of claim 1, wherein said first and second portions of said imaging screen overlap.

6. The x-ray apparatus of claim 1, wherein said first and second portions of said imaging screen overlap by 20%.

7. The x-ray apparatus of claim 1, wherein said first redirecting element is a mirror adapted to redirect light from said first portion onto said second redirecting element.

8. The x-ray apparatus of claim 7, wherein said first redirecting element redirects only a predetermined portion of said light received from said first portion onto said second redirecting element.

9. The x-ray apparatus of claim 1, wherein said second redirecting element is a mirror adapted to redirect light from said first redirecting element onto said first imaging sensor.

10. The x-ray apparatus of claim 1, wherein said first imaging sensor comprises:
    a lens assembly to focus said image received from said first portion of said imaging screen; and
    a photosensitive plate for capturing said image.

11. The x-ray apparatus of claim 10, wherein said photosensitive plate is a CCD chip and said first imaging sensor is a CCD camera.

12. The x-ray apparatus of claim 1, wherein said third redirecting element is a mirror adapted to redirect light from said second portion of said imaging screen.

13. The x-ray apparatus of claim 12, wherein said second subsystem further comprises:
  a fourth redirecting element for redirecting light from said third redirecting element onto said second imaging sensor.

14. The x-ray apparatus of claim 13, wherein said fourth redirecting element is a mirror adapted to redirect light from said third redirecting element onto said second imaging sensor.

15. The x-ray apparatus of claim 1, wherein said second imaging sensor comprises:
  a CCD chip for capturing said image.

16. The x-ray apparatus of claim 10, wherein said multiple redirection of light by said first and second redirecting elements increases an optical path length of light from said first portion.

17. The x-ray apparatus of claim 16, wherein said increase in said optical path length facilitates a corresponding decrease in the length of said lens assembly.

18. The x-ray apparatus of claim 1, wherein utilization of multiple subsystems to capture an image of different portions of said imaging screen increases an optical path length of light from said imaging screen necessary to capture said image.

19. An x-ray apparatus, comprising:
  an x-ray source capable of directing x-rays through an object;
  an imaging screen wherein said object is positioned between said imaging screen and said x-ray source, and wherein said imaging screen is divided into at least two portions;
  a first redirecting element for redirecting a visible portion of light received from a first portion of said imaging screen;
  a second redirecting element for redirecting visible light received from said first redirecting element;
  a first imaging sensor, comprising:
    a lens assembly to focus said light received from said first portion of said imaging screen; and
    a photosensitive plate for capturing a first image of said object;
  a third redirecting element for redirecting a predetermined portion of light received from a second portion of said imaging screen; and
  a second imaging sensor for receiving redirected visible light from said third redirecting element, wherein said second imaging sensor comprises a CCD chip for capturing a second image of said object, wherein said first and second captured images overlap.

20. The x-ray apparatus of claim 19, further comprising:
  a fourth redirecting element for redirecting visible light received from said third redirecting element prior to providing it to said second imaging sensor.

21. The x-ray apparatus of claim 19, wherein said imaging screen is a fluorescent phosphor screen.

22. The x-ray apparatus of claim 19, wherein said first redirecting element is a mirror adapted to absorb x-ray radiation.

23. The x-ray apparatus of claim 19, wherein said second redirecting element is a trapezoidal mirror.

24. A method for capturing an image from an imaging screen, comprising:
  receiving x-rays at an imaging screen;
  converting said x-rays into radiation of at least one selected spectral component at said imaging screen;
  capturing a first image from a first portion of said radiation at a first imaging subsystem; and
  capturing a second image from a second portion of said radiation at a second imaging subsystem, wherein said first image and second image comprise image data associated with a common portion of said imaging screen.

25. The method of claim 24 wherein said at least one selected spectral component is visible light.

26. The method of claim 24 wherein said imaging screen comprises fluorescent phosphor material.

27. The method of claim 24 further comprising:
  directing a portion of said radiation to said first imaging subsystem utilizing a trapezoidal mirror.

28. The method of claim 24 wherein said first imaging subsystem comprises a CCD chip.

* * * * *